(12) United States Patent
Ferrari et al.

(10) Patent No.: US 8,758,430 B2
(45) Date of Patent: Jun. 24, 2014

(54) MEDICAL APPARATUS FOR THE THERAPEUTIC TREATMENT OF AN INSUFFICIENT CARDIAC VALVE

(75) Inventors: Markus Ferrari, Jena (DE); Hans-Reiner Figulla, Jena (DE)

(73) Assignee: JenaValve Technology, Inc., Wilmington, DE (US)

( * ) Notice: Subject to any disclaimer, the term of this patent is extended or adjusted under 35 U.S.C. 154(b) by 249 days.

(21) Appl. No.: 12/863,935

(22) PCT Filed: Jan. 23, 2009

(86) PCT No.: PCT/EP2009/050762
§ 371 (c)(1),
(2), (4) Date: Nov. 12, 2010

(87) PCT Pub. No.: WO2009/092782
PCT Pub. Date: Jul. 30, 2009

(65) Prior Publication Data
US 2011/0106244 A1 May 5, 2011

(30) Foreign Application Priority Data

Jan. 25, 2008 (EP) .................................... 08100963

(51) Int. Cl.
*A61F 2/24* (2006.01)
(52) U.S. Cl.
USPC .......................................................... 623/2.1
(58) Field of Classification Search
USPC .................................................. 623/2.1–2.42
See application file for complete search history.

(56) References Cited

U.S. PATENT DOCUMENTS

| 4,164,046 A | 8/1979 | Cooley |
| 4,261,342 A | 4/1981 | Aranguren Duo |
| 4,806,595 A | 2/1989 | Noishiki et al. |
| 5,332,402 A | 7/1994 | Teitelbaum |

(Continued)

FOREIGN PATENT DOCUMENTS

| WO | WO 00/48531 | 8/2000 |
| WO | WO 2004/019825 A | 3/2004 |
| WO | WO 2008/051554 A | 5/2008 |

OTHER PUBLICATIONS

Bruce, C.J. et al., "Right-sided Valve Disease Deserves a Little More Respect," *Circulation*, vol. 119, No. 20, pp. 2726-2734 (2009).

(Continued)

*Primary Examiner* — Suzette J Gherbi
(74) *Attorney, Agent, or Firm* — Bookoff McAndrews, PLLC (57) ABSTRACT

The present invention relates to a medical apparatus for the therapeutic treatment of an insufficient cardiac valve (3a, 3b). The aim of the present invention is to specify a medical apparatus which enables the therapeutic treatment of an insufficient cardiac valve, such as, for example, the mitral valve (3a) or the tricuspid valve (3b), which is arranged between a ventricle (1a, 1b) and an atrium (2a, 2b) of the heart, in a manner as simple as possible and as gentle as possible for the patient in a minimally invasive intervention. For this purpose, the medical apparatus according to the present invention comprises at least one valve means (10) which is designed to prevent in the implanted condition of the medical apparatus a systolic venous reflex return of blood from the atrium (2a, 2b) of the heart into at least one vein (4a, 4a', 4b, 4b', 4c, 4c') which belongs to a venous system (4) which leads into the atrium (2a, 2b) of the heart.

2 Claims, 5 Drawing Sheets

(56) References Cited

U.S. PATENT DOCUMENTS

| | | | |
|---|---|---|---|
| 5,607,465 A | 3/1997 | Camilli | |
| 5,824,061 A | 10/1998 | Quijano et al. | |
| 5,855,601 A | 1/1999 | Bessler et al. | |
| 5,997,573 A | 12/1999 | Quijano et al. | |
| 6,012,457 A | 1/2000 | Lesh | |
| 6,074,417 A | 6/2000 | Peredo | |
| 6,299,637 B1 | 10/2001 | Shaolian et al. | |
| 6,357,104 B1* | 3/2002 | Myers | 29/527.1 |
| 6,358,277 B1 | 3/2002 | Duran | |
| 6,368,338 B1* | 4/2002 | Konya et al. | 606/200 |
| 6,383,193 B1 | 5/2002 | Cathcart et al. | |
| 6,451,025 B1 | 9/2002 | Jervis | |
| 6,503,272 B2 | 1/2003 | Duerig et al. | |
| 6,569,196 B1 | 5/2003 | Vesely | |
| 6,608,040 B1 | 8/2003 | Lin et al. | |
| 6,610,085 B1 | 8/2003 | Lazarus | |
| 6,676,698 B2 | 1/2004 | McGuckin, Jr. et al. | |
| 6,792,979 B2* | 9/2004 | Konya et al. | 140/92.1 |
| 6,840,957 B2 | 1/2005 | DiMatteo et al. | |
| 6,991,649 B2 | 1/2006 | Sievers | |
| 7,048,014 B2* | 5/2006 | Hyodoh et al. | 140/92.1 |
| 7,611,534 B2 | 11/2009 | Kapadia et al. | |
| 7,704,277 B2 | 4/2010 | Zakay et al. | |
| 2003/0009189 A1* | 1/2003 | Gilson et al. | 606/200 |
| 2003/0078652 A1 | 4/2003 | Sutherland | |
| 2004/0138745 A1 | 7/2004 | Macoviak et al. | |
| 2004/0206363 A1* | 10/2004 | McCarthy et al. | 128/898 |
| 2004/0210306 A1* | 10/2004 | Quijano et al. | 623/2.17 |
| 2004/0236411 A1* | 11/2004 | Sarac et al. | 623/1.26 |
| 2004/0260390 A1 | 12/2004 | Sarac et al. | |
| 2004/0260393 A1 | 12/2004 | Rahdert et al. | |
| 2005/0038509 A1 | 2/2005 | Ashe | |
| 2005/0049692 A1* | 3/2005 | Numamoto et al. | 623/1.24 |
| 2005/0075727 A1 | 4/2005 | Wheatley | |
| 2005/0137682 A1* | 6/2005 | Justino | 623/1.24 |
| 2005/0137689 A1 | 6/2005 | Salahieh et al. | |
| 2005/0143809 A1 | 6/2005 | Salahieh et al. | |
| 2005/0177227 A1 | 8/2005 | Heim et al. | |
| 2005/0267567 A1* | 12/2005 | Shalev | 623/1.31 |
| 2005/0267573 A9 | 12/2005 | Macoviak et al. | |
| 2006/0058871 A1 | 3/2006 | Zakay et al. | |
| 2006/0241745 A1* | 10/2006 | Solem | 623/2.18 |
| 2007/0156233 A1 | 7/2007 | Kapadia et al. | |
| 2007/0185571 A1 | 8/2007 | Kapadia et al. | |
| 2007/0225802 A1* | 9/2007 | Forsell | 623/2.34 |
| 2007/0244545 A1* | 10/2007 | Birdsall et al. | 623/1.26 |
| 2007/0244546 A1* | 10/2007 | Francis | 623/1.26 |
| 2007/0270943 A1 | 11/2007 | Solem et al. | |
| 2008/0133002 A1 | 6/2008 | Gelbart et al. | |
| 2008/0140188 A1 | 6/2008 | Rahdert et al. | |
| 2009/0099643 A1* | 4/2009 | Hyodoh et al. | 623/1.15 |
| 2009/0234407 A1* | 9/2009 | Hastings et al. | 607/14 |
| 2009/0248143 A1 | 10/2009 | Laham | |
| 2010/0069916 A1* | 3/2010 | Cully et al. | 606/108 |
| 2010/0087913 A1* | 4/2010 | Rabkin et al. | 623/1.16 |
| 2011/0166637 A1* | 7/2011 | Irwin et al. | 623/1.13 |
| 2012/0221100 A1* | 8/2012 | Huber | 623/2.17 |

OTHER PUBLICATIONS

Rogers, J.H. et al., "The Tricuspid Valve: Current Perspective and Evolving Management of Tricuspid Regurgitation," *Circulation*, vol. 119, No. 20, pp. 2718-2725 (2009).

Klein, A.L. et al., "Age-related Prevalence of Valvular Regurgitation in Normal Subjects: A Comprehensive Color Flow Examination of 118 Volunteers,". *J. Am. Soc. Echocardiogr.*, vol. 3, No. 1, pp. 54-63 (1990).

Nath, J. et al., "Impact of Tricuspid Regurgitation on Long-term Survival," *J. Am. College of Cardiol.*, vol. 43, No. 3, pp. 405-409 (2004).

Gummert, J.F. et al., "Cardiac Surgery in Germany During 2006: A Report on Behalf of the German Society for Thoracic and Cardiovascular Surgery," *Thorac. Cardiov. Surg.*, vol. 55, No. 6, pp. 343-350 (2007).

Gummert, J.F. et al., "Cardiac Surgery in Germany During 2007: A Report on Behalf of the German Society for Thoracic and Cardiovascular Surgery," *Thorac. Cardiov. Surg.*, vol. 56, No. 6, pp. 328-336 (2008).

Filsoufi, F. et al., "Long-term Outcomes of Tricuspid Valve Replacement in the Current Era," *Ann. Thorac. Surg.*, vol. 80, No. 3, pp. 845-850 (2005).

* cited by examiner

MEDICAL APPARATUS FOR THE THERAPEUTIC TREATMENT OF AN INSUFFICIENT CARDIAC VALVE

This application is a national stage filing under 35 U.S.C. §371 of International Application No. PCT/EP2009/050762, filed on Jan. 23, 2009, which published in the English language and claims the benefit of priority to EP Application No. 08100963.1 filed on Jan. 25, 2008.

The present invention relates to a method and medical apparatus for the therapeutic treatment of a cardiac valve insufficiency.

As the body ages, cardiac valves can become functionally defective, whether through calcification, genetic faults or general weakness. In this way, the valves become stenosed (narrowed), insufficient (unable to close properly) or a combination of the two (combined vitium).

Current treatment for severe valvular insufficiency is replacement of the diseased cardiac valve with a valvular prosthesis. Biological or mechanical valve models are available which are typically surgically stitched (sutured) to the native cardiac valve bed after opening the thorax and removing the native diseased cardiac valve. During such an intervention, the cardiovascular system of the patient has to be supported by a heart-lung machine, with cardiac arrest being induced during implantation of the replacement valvular prosthesis. This involves a risky surgical intervention with corresponding risks for the patient and a long postoperative treatment phase. In particular, patients suffering from cardiac insufficiencies may not be fit or well enough to survive such an invention.

As a result, there is an ongoing effort in the field of medical engineering to find alternative ways to treat valvular heart disease, for example, by transarterial delivery of a replacement prosthesis, thereby avoiding the potentially life-threatening procedures of opening of the thorax dose and inducing cardiac arrest. An additional significant advantage of minimally invasive therapy methods is that a significantly reduced anaesthesia time period is required for the intervention. One approach provides for the implantation of a self-expanding valvular prosthesis in which an artificial cardiac valve is held within a foldable and expandable structure such as a stent. Such a self-expanding valvular prosthesis may be guided by a catheter system, for example through an inguinal artery or inguinal vein, as far as the implantation site in the heart. After the implantation site has been reached, the stent is unfolded and anchored in the position of the native, failing valve. Such a method leaves the native valve in place and provides a replacement valve in place of the native valve.

The above described method is particularly suited for the treatment of diseased semilunar valves, such as the aortic valve or the pulmonary valve, i.e. a cardiac valve that lies between a ventricle and a discharge vessel (aorta or pulmonary artery, respectively).

However, such a method is not readily applicable to the treatment of diseased atrioventicular valves of the heart. Firstly, the atrioventicular valves of the heart, such as the tricuspid valve or the mitral valve, cannot be directly reached with a catheter system via a blood vessel because the valves are located between an atrium and ventricle of the heart. In addition, both the mitral valve and the tricuspid valve belong to a valve type which comprises two or three, respectively, relatively delicate, fibrous cusps which are attached via tendinous fibres to the papillary muscles which face the ventricle.

Due to these anatomic facts, therapeutic treatment of mitral or tricuspid valve insufficiency is presently not possible by means of the currently available minimally invasive replacement approaches.

Therefore, such insufficiencies are typically treated with a long-term drug treatment including ACE blockers and often require additional anti-arrhythmia treatment. This pharmaceutical approach is based on the finding that patients with a "real", i.e. not only a physiological mitral or tricuspid insufficiency, are at an increased risk of bacterial endocarditis.

Operative therapy is available in which the insufficient cardiac valve is either reconstructed or an artificial cardiac valve is inserted. This, however, entails risky surgical intervention with corresponding risks for the patient and a long postoperative treatment phase. Moreover, such an invention cannot be performed on patients suffering from other cardiac insufficiencies. Therefore, operative therapy of a mitral or tricuspid insufficiency is performed only seldomly.

Accordingly, the present invention arises from the problem of providing a medical apparatus which is suited for the therapeutic treatment or replacement of an atrioventricular (mitral or tricuspid) valve insufficiency in such a way that the drawbacks and risks associated with the currently available options are substantially eliminated. Such a medical apparatus should enable the therapeutic treatment or replacement of an insufficient atrioventricular valve in a manner that is as simple and as gentle as possible for the patient with minimally invasive intervention.

This object is solved by a medical apparatus for the therapeutic treatment of an insufficient cardiac valve which is arranged between a ventricle and an atrium of the heart, with the medical apparatus according to invention comprising at least one valve which is designed to prevent in the implanted condition of the medical apparatus a systolic venous reflex return of blood from the atrium of the heart into at least one vein which belongs to a venous system which leads into the atrium of the heart. Specifically, the apparatus is suitable for the treatment of an insufficient atrioventricular valve located between a heart ventricle and atrium, the apparatus comprising at least one pair of valves. Ideally each valve in the pair of valves is directionally opposed to the other valve in the pair.

It is generally known from the medical science that, in the case of a severe mitral insufficiency or tricuspid insufficiency, serious and sometimes life-threatening changes have to be expected if, for example, the regurgitation opening is greater than 40 $mm^2$ and the regurgitation volume more than 60 ml. Specifically, in the acute stage of a mitral insufficiency or tricuspid insufficiency, the pressure in the atrium of the heart and thus in the veins of the venous system which lead into the atrium of the heart will increase considerably due to the systolic reflex return of blood. With a tricuspid valve insufficiency, the pressure increase in the right-hand atrium of the heart may amount up to 50 mm Hg which, with a normal constitution of the venea cavae (superior and inferior vena cava), results in immediate congestion in the liver or a venous congestion into the cervical vein. In addition, the then dominating reflex return of blood may cause a poor output into the pulmonary artery and thus inadequate circulation to all organs. In the case of a severe mitral insufficiency, the pressure increase in the left-hand atrium of the heart may amount up to even 100 mm Hg which, with normal constitution of the pulmonary vessels, leads to immediate pulmonary oedema. In addition, the reflex return of blood may result in poor output into the aorta and thus again inadequate circulation to all organs.

The inventive solution is based on the finding that, due to the anatomic peculiarities of the mitral and tricuspid valves— collectively termed "atrioventicular valves"—a minimally invasive replacement of an insufficient atrioventicular valve where the diseased atrioventicular valve is replaced by an artificial valvular prosthesis, is not possible or possible only at high risk. In the present invention it has been found that, for the treatment of a mitral or tricuspid valve insufficiency, it is not mandatory to replace the diseased cardiac valve with a valvular prosthesis. Indeed, it is sufficient to provide a replacement apparatus by means of which the normal valve function of the insufficient atrioventicular valve can be maintained.

Consequently, the proposed inventive solution will combat a more or less pronounced closure inability or leakiness of a diseased atrioventicular valve of the heart. In particular, the medical apparatus effectively prevents reflex return of blood from the ventricle into the atrium during the output phase (systole) such that regurgitation of blood into the venous system can no longer occur. The proposed medical apparatus of the present invention is therefore used for the therapeutic treatment of an insufficient atrioventicular valve or an insufficient cardiac valve which is arranged between a ventricle and an atrium of the heart, whereby it is not the diseased cardiac valve itself that is treated or replaced but an implant is used which is functionally matched to the diseased cardiac valve. This implant is designed to at least partially fulfil or support the function of the insufficient cardiac valve without the diseased cardiac valve being replaced or mechanically modified.

Due to the fact that the function of the diseased or insufficient cardiac valve is restored by means of an implant, systolic regurgitation of blood from the atrium of the heart into the veins which lead into the atrium can be effectively prevented. The proposed solution can thus effectively counteract the danger of congestion in the liver or venous congestion in the cervical vein, in the case of a tricuspid insufficiency, or the danger of a pulmonary oedema in the case of a mitral insufficiency. Due do the fact the proposed medical apparatus serves to restore the normal function of the cardiac valve, there is little need to implant the medical apparatus into the immediate vicinity of the diseased cardiac valve. In contrast, the implantation site of the medical apparatus is spatially separated from the site of the insufficient cardiac valve that is to be treated.

Specifically, it is provided according to the invention that the medical apparatus comprises at least one pair of valves that is dimensioned for location in a vena cava or pulmonary vein. Expressed in another way, the at least one valve is implanted either into the atrium of the heart which is separated from the ventricle via the diseased cardiac valve, or is implanted into at least one of the veins belonging to the venous system which leads into the atrium which is separated from the ventricle via the diseased cardiac valve, or is implanted into the pulmonary veins draining blood from the pulmonary circulation into the left atrium (An implantation through the vein is preferred; however, an implantation using an arterial access (retrograde) is also possible).

The term "venous system" as used herein refers to the group of veins which lead into the heart atria. When the tricuspid valve, located between the right-hand atrium of the heart and the right-hand ventricle, is to be treated, the venous system is thus the superior (upper) vena cava and the inferior (lower) vena cava. If the cardiac valve to be treated is the mitral valve, which is located between the left-hand atrium of the heart and the left-hand ventricle, the venous system generally comprises four pulmonary veins through which oxygen-rich (arterial) blood from the pulmonary circulation flows to the left-hand atrium of the heart.

The inventive solution for the therapeutic treatment of an insufficient cardiac valve which is arranged between a ventricle and an atrium of the heart proposes a medical apparatus which comprises at least one valve, ideally at least one pair of valves which, in the implanted condition, serves to and is designed to prevent a systolic venous reflex return of blood from the atrium of the heart into at least one vein belonging to the venous system which leads into the atrium. Due to the fact that the valve of the medical apparatus is designed to prevent the regurgitation of blood into the associated venous system, which occurs with an insufficient mitral valve or tricuspid valve, it is possible to implant the at least one valve away from the immediate vicinity of the insufficient cardiac valve, in the or in the vicinity of the atrium of the heart which is separated from the ventricle via the insufficient cardiac valve.

Because the veins of the venous system which leads into the atrium of the heart are normally well suited for probing by means of catheters, a medical apparatus is proposed by the inventive solution by means of which the at least one valve or pair of valves can be implanted in a minimally invasive manner. The proposed medical apparatus thus enables a minimally invasive therapeutic method which, in particular, excels in that the intervention may be performed under local anaesthesia. It would be conceivable to implant the valves of the medical apparatus in a folded condition via a corresponding catheter system into the atrium of the heart or in the respective veins of the venous system which leads into the atrium of the heart. Such self-expandable valves may be guided through a peripheral artery or a peripheral vein as far as the implantation site in the heart by means of a catheter system. The peripheral artery or vein can be an inguinal, jugular or subclavian artery or vein. After the implantation site has been reached, the valves may be unfolded. After unfolding, the valves may be anchored at least in the atrium-near area of the respective veins of the venous system by means of anchoring hooks, barbs or sutures.

As suitable valves, various natural, biological or mechanical valve models may be taken into consideration. For example, a natural arterial valve, such as a semilunar valve, may be used. These may be either surgically sutured to the vascular wall of the vein or attached in another suitable manner. It would also be conceivable that the valves of the medical apparatus are held in the implantation site by means of a support, such as a suitable stent. Thereby, it is of importance that the valves substantially prevent systolic reflex return of blood from the atrium of the heart into the associated vein of the venous system.

As a possible realisation of the valves, a pressure driven check valve may be considered which is designed automatically to block the through-flow of blood from the atrium during the systole into at least one associated vein. A check valve is a valve that allows fluid to flow through it in only one direction. Check valves are two-port valves, meaning they have two openings in the body, one for fluid (e.g. blood) to enter and the other for fluid (e.g. blood) to leave.

Regardless of the valve model which is employed as a valve, it should be noted that, during implantation of the valves, it is not necessary to support the cardiovascular system of the patient on a heart-lung machine. In particular, it is no longer necessary to induce a cardiac arrest during the procedure. The therapeutic treatment of an insufficient cardiac valve (atrioventicular valve) which may be achieved with the inventive medical apparatus thus also comprises an instrument which may be operated in a relatively easy manner and which is capable of being implanted in a minimally invasive intervention without a long postoperative treatment phase. Such an intervention is also possible for polypathic patients at a justifiable risk.

As valves for the inventive medical apparatus, models may be chosen which comprise mechanic valve flaps manufactured from a biologic or synthetic material, or native valve flaps taken from natural arterial valves. In particular, it would be conceivable to make the valve flaps from metal, synthetic material, or animal tissue. Valve flaps made from endogenous tissue are, of course, also conceivable. Such valve flaps have the decisive advantage that no (higher) risk of embolism exists so the patient should not need to be prescribed anti-coagulant medication. It is known that the administration of anti-coagulants increases the danger of bleeding from the stomach and cerebral bleedings and so is an undesirable outcome.

As already mentioned, a plurality of veins belongs to the venous system lead into the atria of the heart. Specifically, the venous system which leads into the right-hand atrium comprises the superior and inferior vena cava, via which deoxygenated (venous) blood from the systemic circulation is supplied to the heart. The tricuspid valve separates the right atrium from the right ventricle. On the other hand, generally four pulmonary veins belong to the pulmonary system lead into the left-hand atrium of the heart, which is separated from the left-hand ventricle via the mitral valve. For an effective therapeutic treatment of an insufficient cardiac valve which is arranged between a ventricle and an atrium of the heart it is mandatory that a systolic reflex return of blood into each single vein of the venous system which leads into the atrium of the heart is prevented by means of the medical apparatus. For this purpose it would be conceivable that the at least one valve means of the medical apparatus is correspondingly designed and dimensioned for simultaneously preventing a regurgitation of blood from the atrium of the heart into several veins of the venous system. This seems to be obvious, in particular, if the veins of the venous system are arranged in a neighbouring relationship as in the case of the venous system which leads into the left-hand atrium of the heart. In this venous system, two pulmonary veins extend almost in parallel into the left-hand atrium of the heart so that a systolic reflex return of blood from the left-hand atrium of the heart into these two parallel pulmonary veins may be prevented by a single valve means, in that said valve means covers the mouth area of both pulmonary veins.

For anatomic reasons, however, it is not possible that a single valve always covers several veins of a venous system simultaneously. This applies in particular in those cases in which the respective mouth areas of the veins into the atrium of the heart are relatively remote from one another. In the right-hand atrium of the heart, for example, the upper vena cava enters the top of the atrium, while the mouth of the lower vena cava is located almost opposite in the lower portion of the atrium. In such a case it is preferred that the medical apparatus comprises a correspondingly assigned valve for each vein which leads into the atrium, with the dimension of the respective valve being matched to the diameter of the associated vein.

As already mentioned, it is conceivable to attach the valves of the medical apparatus after its implantation by means of threads, hooks, barbs or clamps at the vascular wall of a vein. Alternatively, one or several stents might be provided for the attachment of the valves at the implantation site(s). Such stents may preferably be inserted into the body of the patient in a minimally invasive manner and may either be implanted or fixed a vein of the venous system or in the atrium of the heart into which the vein leads. The at least one valve should be attached inside the stent or in a proximal retention area of the stent.

If the medical apparatus comprises a stent which serves to and is designed to be implanted into a vein of the venous system leading into the atrium of the heart, preferably near the mouth area of the vein into the atrium of the heart, it would be conceivable to attach the valve in a central area of the stent. In this way, stable and reliable anchoring of the valve is ensured. It is, of course, also conceivable that the at least one stent of the medical apparatus is designed in such a manner that, in the implanted condition, it extends only partially into the vein and is held by the vascular wall of the area near the mouth of the vein, while the proximal end portion of the stent protrudes into the atrium of the heart with the valve being attached at the proximal end portion of the stent.

It is principally applicable that the valve should be arranged relative to the stent and connected in such a manner that, in the implanted condition of the stent, the valve is able effectively to prevent regurgitation of blood from the atrium of the heart into the at least one associated vein.

In a further embodiment of the inventive apparatus which comprises at least one stent for holding and fixing each valve, it is advantageous to provide the at least one stent with an expandable structure. Ideally, the diameter of the at least one stent in its expanded condition is matched to the diameter of the vein in which the stent is to be implanted. Due to its preferably expandable structure, the stent in its folded condition may be advanced via a catheter system in a minimally invasive manner to the implantation site in the heart. After having reached the implantation site, the stent which, in the longitudinal direction, may also be composed of several stent segments which may be bent under an angle relative to one another and are self-expanding, may be successively unfolded. After unfolding, the valve may be attached to or inside the stent, for example with the aid of fastening hooks, in the area near the mouth of the appropriate vein.

It is, of course, also conceivable that the valve is already securely connected with the stent and able to be folded together with the stent in order to enable the implantation of these two systems.

Because the stent in its expanded condition is matched to the diameter of the vein to the stent is assigned, it is possible to hold the stent reliably together with the valve, the valve be attached or attachable to the stent without additional auxiliary means at the site of implantation. It is advantageous if the stent in its implanted and expanded condition presses against the vascular wall of the vein with a relatively small radially acting force. This radially acting force serves to hold the stent reliably in its implanted position. In the design of the stent, on the other hand, care should be taken not to use an excessive radial force to avoid damage to the vascular wall of the vein.

To enable a reliable fixing of the stent at the site of implantation, it is possible to provide the stent with a plurality of distributed anchoring hooks or barbs on its outside which, in the implanted condition of the stent, engage with the vascular wall of the vein assigned to the stent and thus ensure an especially reliable anchoring of the stent.

For the at least one stent of the inventive medical apparatus, various stent types may be considered, including stents formed from a braid of thin wires or threads. Stent types which are cut as one piece from a small metal tube and then appropriately treated are, of course, also suitable. As the material for the stent, the usual solutions which are known from medical engineering may be taken into consideration. In particular, however, a shape memory material, such as nitinol or a shape memory polymer material, is a preferred choice, so that the stent comprises a self-expandable structure. It is, of course, also possible to form the stent from a material which has no shape memory capability. With such a stent type, the expansion of the stent in the implantation site is to be effected by an external manipulation, for example by using a balloon catheter.

As already mentioned, the medical apparatus should preferably comprise a plurality of valves, with each valve being assigned to a vein of the venous system which leads into the atrium. If the medical apparatus comprises at least one stent for establishing the position of the valve in the venous system or in the atrium of the heart and for anchoring the valve in the implantation site, it is advantageous if the medical apparatus comprises for each vein one stent with an attached or attachable valve. The respective stents are capable of being implanted either successively or simultaneously into the venous system by means of one and the same catheter system.

It is advantageous to connect the individual stents of the medical apparatus to each other via one or more supporting braces. These supporting braces may already be connected with the individual stents prior to implantation of the individual stents. However, it is also possible to arrange and attach the supporting braces after the implantation of the individual stents. In the implanted condition of the medical apparatus, the supporting braces extend through the atrium of the heart and preferably connect the respective proximal end portions of the individual stents The provision of such supporting braces ensures a particularly reliable fixing of the stents in the respective veins of the venous system. The supporting braces primarily serve to secure the relative position of the individual stents in their respective implanted positions. In this context, it has to be taken into consideration that, due to the insufficient cardiac valve, blood flows back into the atrium of the heart upon the contraction of the heart, resulting in a pressure increase in the atrium. Because regurgitation of blood from the atrium into the individual veins leading into the atrium is substantially prevented with the aid of the respective valves, it is important that the individual valves are reliably fixed, especially during systole, and are not urged in the distal direction into the vein due to the increased pressure in the atrium of the heart. This may be prevented very effectively by way of the supporting braces.

It is, of course, also conceivable that the supporting braces have a certain flexural rigidity to counteract any displacement of the individual stents in the proximal direction, i.e. towards the atrium of the heart.

As an alternative to the previously described embodiment in which the medical apparatus comprises a stent with a valve for each vein of the venous system, it would be conceivable that the medical apparatus comprises only one stent which is formed from different stent portions. It might be conceivable that a first stent portion of the stent is provided and designed or adapted with a first valve for the implantation into a first vein of the venous system, with the stent further comprising a second stent portion with a second valve. This second stent portion may be designed and adapted to be inserted into a second vein of the venous system. The two stent portions are preferably connected with one another via at least one supporting brace.

The advantage of the last mentioned embodiment lies in the fact that the stent with its stent portions and the associated valve can be implanted as a single implant using a single intervention procedure.

In the last mentioned embodiment it is, of course, also possible that the stent further comprises a third and a fourth stent portion with third and fourth valves which are designed and adapted to be inserted into a corresponding third and fourth vein of the venous system.

In a preferred embodiment of the medical apparatus, in which at least one stent for holding and fixing the valve is employed, at least one stent may be capable of being implanted into the vein system which leads into the atrium of the heart in such a manner the at least one valve is located at the proximal end portion of the stent in the atrium of the heart. This valve should be designed to prevent simultaneously regurgitation of blood from the atrium of the heart into at least two veins of the venous system. This preferred embodiment is suitable for relatively closely-spaced veins which lead into the atrium of the heart. In such a case, a bifurcated stent may be used which engages the mouth area of both veins and abuts the vascular wall of the respective veins where it is held. Thus, the distal end portion of the stent protrudes into the mouth area of a first vein, on the one hand, and into the mouth area of a second vein. At the proximal end portion, a valve is arranged and held so that this valve covers the mouth areas of both veins and thus prevents regurgitation of blood from the atrium into both veins.

It will be apparent that the medical apparatus of the present invention is designed to correct a faulty valve function of an insufficient cardiac valve, in particular a mitral valve or a tricuspid valve, in a minimally invasive intervention. In order to enable a suitable implantation of the medical apparatus and, in particular, of the corresponding valve optionally with a stent, the medical apparatus further resides in an insertion system for inserting the at least one stent with the valve attached thereon into the body of the patient. The insertion system may comprise a catheter system with a catheter tip provided at the proximal end of the catheter system and a manipulator provided at the distal end of the catheter system. The at least one stent with the at least one valve attached is preferably designed to be expandable and may be accommodated in the catheter tip in a folded configuration. In this manner, the at least one stent, in its folded configuration, can be inserted into body of the patient. The manipulator provided at the distal end of the catheter system may be used to manipulate the catheter tip, via which the at least one stent is released and the stent and valve implanted.

After release of the stent from the catheter tip, the stent assumes an expanded condition, either automatically or with the aid of a suitable auxiliary means such as a balloon catheter, and is anchored at the implantation site.

It is particularly preferred to use an insertion system by means of which at least one stent with the valve attached thereon can be advanced through the vena cava or through a pulmonary vein of a patient to be treated (retrograde or transarterial). Alternatively, the implantation site may be accessed through the apex of the heart (transapical). With transarterial access, the insertion catheter system preferably does not completely fill the free cross-section which is available within the vein.

From a yet further aspect, the present invention resides in a method of replacing an insufficient atrioventricular valve located between a heart ventricle and atrium, the method comprising implanting, at a position proximate to the atrium, one or more pairs of valves in a vein that feeds directly into the atrium.

Expressed in another way, the invention encompasses the use of one or more pairs of valves substantially to replace or enhance the function of an insufficient atrioventricular valve located between a heart ventricle and atrium, wherein the valves are implanted in one or more veins at a position proximate to the atrium.

The method also encompasses the treatment of an insufficient atrioventricular valve located between a heart ventricle and atrium by venous implantation of at least one pair of valves proximate to the atrium.

Alternatively, the invention resides in the enhancement of tricuspid and/or mitral valve function by the use of at least one pair of valves venously implanted at a position proximate to a heart atrium.

Ideally, each valve in the pair of valves is directionally opposed to the other valve in the pair.

As described above, the vein is the vena cava or pulmonary vein. For example, a pair of valves may be implanted in the superior and inferior vena cava respectively, proximate to where the venae cavae join the right atrium. In this respect, the valve in the superior vena cava substantially prevents blood flow from the right atrium into the superior vena cava and the valve in the inferior vena cava substantially prevents blood flow from the right atrium into the inferior vena cava.

Alternatively, two pairs of valves may be implanted in pulmonary veins proximate to where the veins join the left atrium. In this embodiment, each valve substantially prevents blood flow from the left atrium in the pulmonary vein.

In the following, preferred embodiments of a medical apparatus for the therapeutic treatment of an insufficient cardiac valve located between a ventricle and an atrium of the heart will be described in more detail with reference to the accompanying drawings; in which.

The heart is divided into left and right sides. The function of the right side is to collect de-oxygenated blood, in the right atrium $2b$, from the body and pump it, via the right ventricle $1b$, into the lungs. The left side collects oxygenated blood from the lungs into the left atrium $2a$. From the left atrium $2a$ the blood moves into the left ventricle $1a$ which pumps the blood out to the body.

Starting in the right atrium $2b$, deoxygenated blood flows into the atrium $2b$ from the superior and inferior vena cava $4a$, $4a'$. The tricuspid valve $3a$, located between the right atrium $2b$ and right ventricle $1b$, is open due to the increased pressure in the atrium $2b$ and blood flows into the right ventricle $1b$. Atrial systole causes increased pressure in the atrium $2b$ and added blood flow into the ventricle $1b$. Pressure in the ventricle $1b$ then rises and soon eclipses the pressure in the atrium $2b$, closing the tricuspid valve $3a$. The pressure in the ventricle $1b$ continues to rise until the pressure in the ventricle $1b$ is greater that the pressure in the pulmonary artery 7. This causes the pulmonary semilunar valve $8a$ to open, allowing blood to eject into the pulmonary artery 7 which carries the blood to the lungs. As pressure in the ventricle $1b$ drops to below the pressure in the atrium $2b$, the tricuspid valve $3a$ opens, causing blood accumulated in the atrium $2b$ to flow into the ventricle $1b$.

From the lungs, blood flows back through the pulmonary vein $4b$, $4b'$ to the left atrium $2a$. The mitral (also termed "bicuspid") valve $3b$ regulates the flow of blood into the left ventricle $1a$, from where the blood is pumped through the aortic semilunar valve $8b$ to the aorta 6. The aorta 6 forks and the blood is divided between major arteries which supply the upper and lower body.

Figure 1:
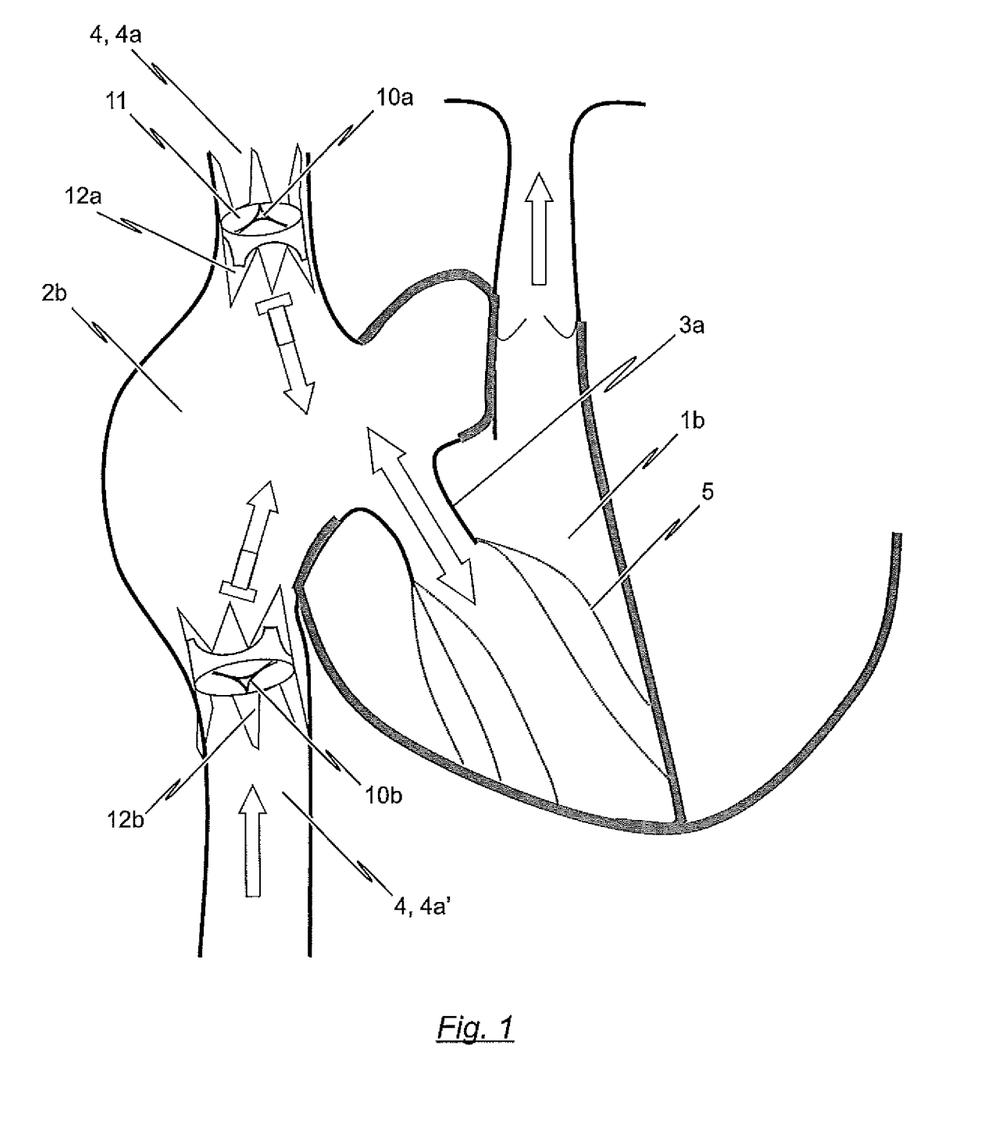
FIG. 1 is a schematic view of a first embodiment of the inventive medical apparatus, which is specifically suited for the therapeutic treatment of a tricuspid insufficiency.

FIG. 1 shows a schematic view of a first embodiment of the inventive medical apparatus for the therapeutic treatment of a tricuspid insufficiency. More specifically, FIG. 1 schematically shows a longitudinal section of a human heart. In this embodiment, the insufficient atrioventricular valve which is to be treated by means of the medical apparatus is the tricuspid valve $3a$, located between the right-hand atrium $2b$ of the heart and the right-hand ventricle $1b$.

The tricuspid valve $3a$ consists of three relatively delicate, fibrous cusps which originate from the right-hand anulus fibrosus. The cusps of the tricuspid valve $3a$ are attached by tendinous fibres 5 (chordae tendineae) to three papillary muscles which face the right-hand ventricle $1b$. Tricuspid valves may also occur with two or four leaflets and the number may change during life. The largest cusp is interposed between the atrioventricular orifice and the conus arteriosus and is termed the anterior or infundibular cusp. A second, the posterior or marginal cusp, is in relation to the right margin of the ventricle. A third, the medial or septal cusp, to the ventricular septum. A small amount of leakage or regurgitation is not uncommon in the tricuspid valve.

The schematic illustration of FIG. 1 concerns a tricuspid insufficiency in which the tricuspid valve $3a$ no longer closes correctly, completely or sufficiently during the systolic phase of the heart beat. Due to the leakiness (regurgitation opening) of the valve, when the heart contracts during systole, blood from the right-hand ventricle $1b$ is able to flow back into the right-hand atrium $2b$, as schematically indicated by the double arrow in FIG. 1. With a severe tricuspid insufficiency, the regurgitation opening may be larger than 40 mm$^2$ and the regurgitation volume more than 60 ml, which results in a considerable increase in pressure in the right-hand atrium $2b$. In this context, it should be noted that a pressure of normally approx. 4 mm Hg prevails in the atrium while, with a severe tricuspid insufficiency, the pressure may be as high as 50 mm Hg.

The superior (upper) and inferior (lower) venae cavae $4a$, $4a'$ carry blood from the cervical vein and liver respectively. Therefore, it is imperative that there is no backflow of blood in either vena cava $4a$, $4a'$. If the tricuspid valve $3a$ is not able to close properly, when the right ventricle $1b$ contracts during systole, there is a risk that blood will be pushed backwards into the right atrium $2b$, through the partially closed tricuspid valve $3a$, and into the venae cavae $4a$, $4a'$. It will be appreciated that this could lead to congestion in the liver and a venous congestion into the cervical vein. To prevent backflow into the venae cavae $4a$, $4a'$ in such a situation, a pair of directionally opposed valves $10a$ and $10b$ may be implanted in the venae cavae $4a$, $4a'$ at a position proximate to where the venae cavae $4a$, $4a'$ enter the right atrium $2b$. The two valves $10a$, $10b$ are preferably pressure driven check valves designed to block automatically the throughflow of blood during the systole of the heart from the right-hand atrium $2b$ of the heart into the upper vena cava $4a$ or into the lower vena cava $4a'$ of the venous system 4.

The valves 10 which are illustrated in the embodiment shown in FIG. 1, function like a valve between the right-hand atrium $2b$ and the two venae cavae (upper vena cava $4a$, lower vena cava $4a'$) leading into the right-hand atrium $2b$. The valves 10 open during the filling phase of the ventricle (diastole), thereby enabling the inflow of blood from the venous system 4 into the right-hand atrium 2b. At the beginning of the output phase (systole), the increasing pressure in the ventricle also results in a pressure increase in the right-hand atrium 2b due to the regurgitation opening in the defective tricuspid valve 2a. Because the valves 10 are formed as pressure-driven check valves, the pressure increase in the right-hand atrium 2b at the beginning of the output phase causes the closure of the valve flaps 11 of the valves 10, thereby sealing the upper and lower vena cava 4a, 4a' from blood flowing in the wrong direction. In this manner, a pressure increase in the venae cavae 4a, 4a' is prevented during the systole. In fact, because of the implanted medical apparatus, a pressure of only approx. 4 mm Hg prevails in the venae cavae 4a, 4a' also during the systole, while at the same time a pressure exceeding 50 mm Hg may prevail in the right-hand atrium 2b because of the regurgitation opening in the defective tricuspid valve 3a.

It is therefore possible to treat a tricuspid insufficiency effectively with the medical apparatus according to the present invention, namely in that the poor or faulty valve or closing function of the tricuspid valve 3a is corrected by the valve means 10a, 10b of the medical apparatus.

In the following, the technical details of the first embodiment of the inventive medical apparatus illustrated in FIG. 1 will be explained in more detail.

In the first embodiment according to FIG. 1, the medical apparatus comprises a pair of valves 10a, 10b which—as already mentioned—are preferably formed as one-way pressure-driven valves. The valves 10a, 10b may be fixed in position, in the respective mouth areas of the upper and lower vena cava 4a, 4a', by any suitable means including thread (sutures), barbs or a clamping mechanism. While not essential, the valves 10a, 10b may each be supported by a stent 12a, 12b. The application is not limited by the type of stent and any suitable stent, including those described, for example, in DE 10 2005 051 849 A1, U.S. Pat. No. 6,254,564 B, US 2003-0036791 A1 or WO 2004/019825, may be used.

The stents 12 which are illustrated in the accompanying drawings are self-expandable stents throughout, in whose central area or at the proximal end portion at least one valve 10 each is suitably fastened. The two stents 12a, 12b in FIG. 1 serve to hold and fix the valves 10a, 10b in the mouth area of the venae cavae 4a, 4a' which leads into the right-hand atrium 2b. It is advantageous if a stent type is employed which in the expanded condition has a diameter which is at least equal to the diameter of the vena cava 4a, 4a' into which the stent 12a, 12b with the valves 10a, 10b fastened thereon is to be implanted.

It is principally applicable that the stents 12a, 12b in the expanded condition should preferably have a diameter each which is slightly larger than the cross-section of the associated vena cava 4a, 4a' for reliably fixing the valves 10a, 10b. It is then possible that, after unfolding of the stent 12, it exerts a (small) radial force on the vascular wall of the vena cava 4a, 4a' by means of which the stent 12a, 12b can be held in position. It is, of course, also conceivable that the stents 12a, 12b include one or several anchoring hooks or barbs which are distributed on their outer surfaces and which, in the expanded and implanted condition the stents 12a, 12b, engage with the vascular wall of the vena cava 4a, 4a' and thus ensure reliable fixing of the stents 12a, 12b.

To achieve a particularly reliable anchoring of the stents 12a, 12b in the respective vena cava 4a, 4a', it is preferred that the stents 12a, 12b in the manufacturing process are subjected to a forming and heat treatment process so that, in the finished condition of the stents 12a, 12b, they have a slightly concave structure in the expanded condition which tapers towards the proximal retention area. In other words, the proximal retention area of the stents 12a, 12b, i.e. the area where the valves 10a, 10b are preferably fastened, comprises a slightly tapered diameter compared to the distal retention area.

Specifically, it was found that where the distal retention area of the stent 12a, 12b in its expanded condition has a diameter of up to approx. 10% to 25% larger than the diameter of the proximal retention area of the stent 12a, 12b, in particular in the distal retention area of the stent 12a, 12b, radial forces are generated which enable a reliable grip of the stent 12a, 12b with the valves 10a, 10b and thus the medical apparatus in the vena cava 4a, 4a'. Peristaltic movement of the heart or of the vascular wall is also taken into account. The slightly lower radial force which is exerted from the proximal retention area of the stent 12a, 12b does not serve primarily to anchor the stent 12a, 12b or the valve 10a, 10b in the vena cava 4a, 4a', but to expand the valves 10a, 10b which are preferably arranged near the proximal retention area of the stent 12a, 12b and for reliably sealing the valve against the vascular wall. It will be appreciated that the concave structure of the stent 12a, 12b in the expanded condition may be more or less pronounced.

For the implantation of the medical apparatus according to the first embodiment, the stents 12a, 12b with the valves 10a, 10b fastened thereon are guided via a suitable insertion catheter system through an inguinal artery or vein as far as the implantation site, namely the mouth area of the upper or lower vena cava 4a, 4a' of the right-hand atrium 2b. Having reached the implantation site, the stents 12a, 12b may then be successively unfolded. Simultaneously with the unfolding of the stent 12a, 12b, the valves 10a, 10b with their valve flaps 11 are expanded.

Because an effective treatment of a tricuspid valve insufficiency requires the provision of one valve 10a or 10b, respectively, in each mouth area of the two venae cavae 4a, 4a' which lead into the right-hand atrium 2b, it is necessary to advance the two valves 10a, 10b with their associated stents 12a, 12b to which the valves 10a, 10b are fastened, successively into their respective implantation sites. It would, of course, also be possible simultaneously to insert and successively unfold both stents 12a, 12b by means of the insertion catheter system.

Figure 2:
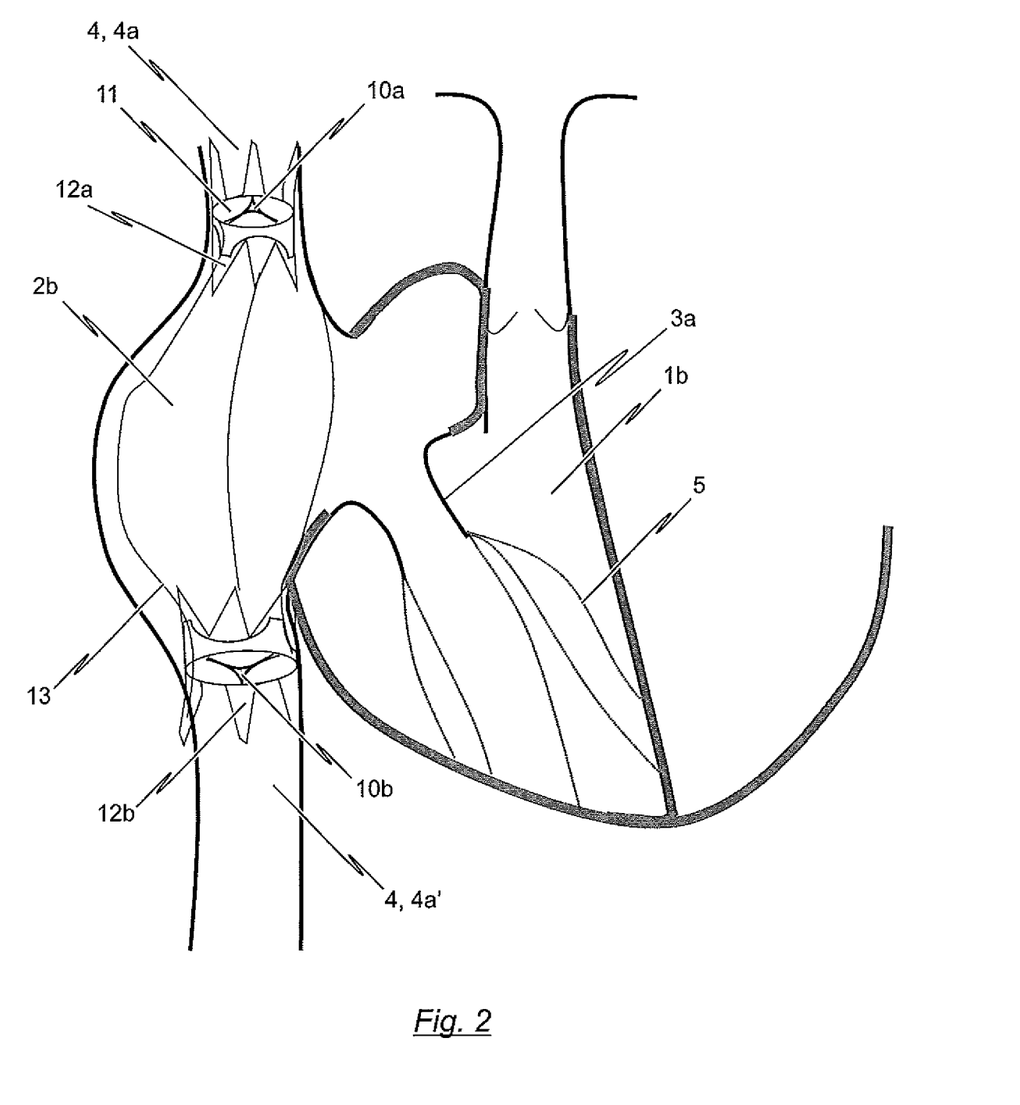
FIG. 2 is a schematic view of a second embodiment of the inventive medical apparatus, which is specifically suited for the therapeutic treatment of a tricuspid insufficiency.

FIG. 2 is a schematic illustration of a second embodiment of the medical apparatus for the treatment of a tricuspid valve insufficiency. The second embodiment of the medical apparatus is essentially identical to the first embodiment with the exception of the addition of supporting braces 13 which connect the respective proximal retention portions of the two stents 12a, 12b with one another. The supporting braces 13 serve to fix the two stents 12a, 12b, and thus the valves 10a, 10b, in a particularly reliable manner.

In this context is has to be taken into consideration that, due to the regurgitation opening in the tricuspid valve 3a, blood returns into right-hand atrium 2b of the heart during the contraction of the ventricle (systole), resulting in a marked pressure increase in the right-hand atrium 2b. Because the valves 10a, 10b of the medical apparatus are designed to close automatically during the output phase (systole), there is a risk that the valves 10a, 10b with the associated stents 12a, 12b may be urged in the distal direction into the respective vena cava 4a, 4a' due to the considerable pressure increase in the right-hand atrium 2b. To ensure that minimal positional displacement of the valves 10a, 10b of the medical apparatus occurs during the systole, the supporting braces 13 between the proximal retention areas of the two stents 12a, 12b are biased, so that the relative distance between the two stents 12a, 12b can reliably be maintained.

The supporting braces 13 may be installed after the implantation of the two stents 12a, 12b into their respective implantation site at the mouth area of the upper or lower vena cava 4a, 4a'. It is also conceivable that the medical apparatus is implanted with the stents 12a, 12b already connected via the supporting braces 13.

Figure 3:
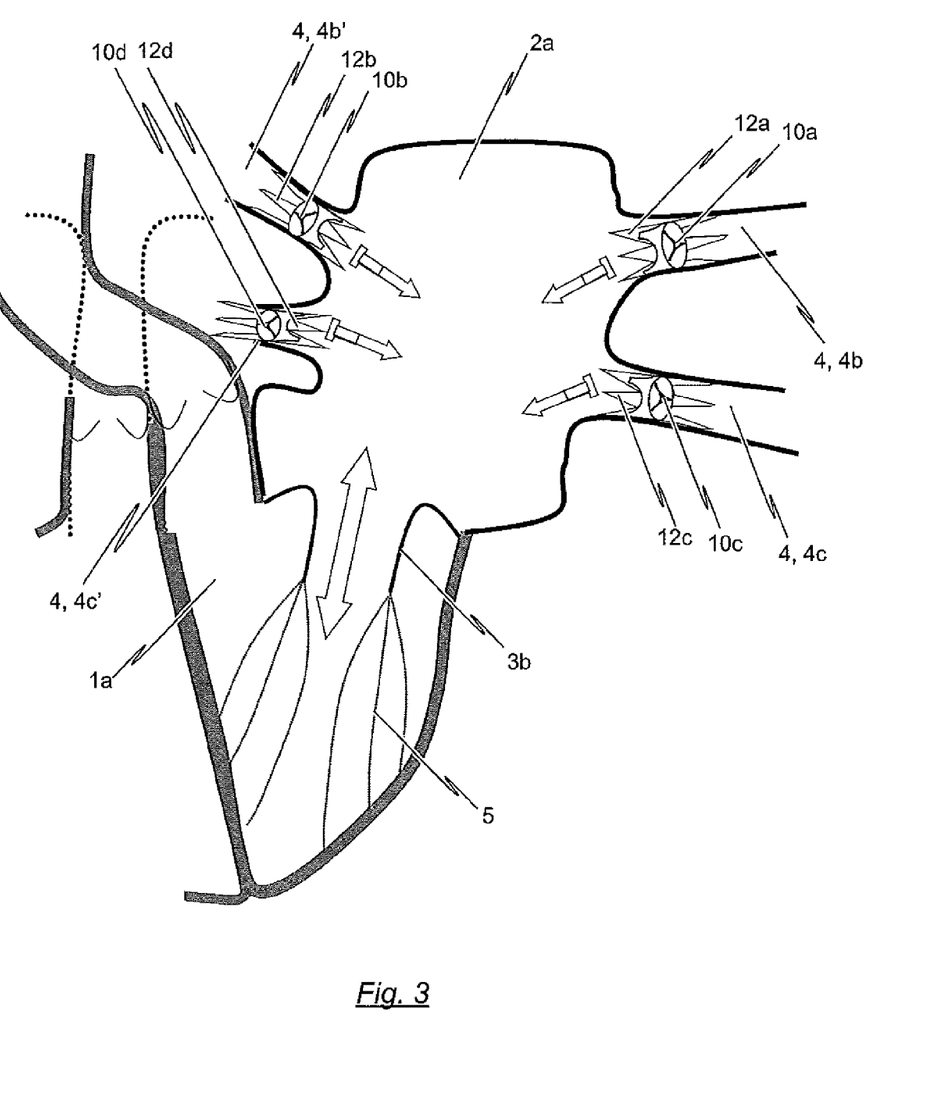
FIG. 3 is a schematic view of a third embodiment of the inventive medical apparatus, which is specifically suited for the therapeutic treatment of a mitral insufficiency.

In the following, a third embodiment of the present invention will be described with reference to FIG. 3. The schematic illustration of FIG. 3 shows an embodiment of the medical apparatus for the therapeutic treatment of a mitral valve insufficiency. As can be seen, the insufficient mitral valve 3b is disposed between the left-hand ventricle 1a and the left-hand atrium 2a. In the case of a mitral valve insufficiency, the mitral valve 3b does not close correctly so that blood from the left-hand ventricle 1a is able to flow back into the left-hand atrium 2a during systole. Depending on the regurgitation opening as a result of the mitral insufficiency, a considerable pressure increase occurs in the left-hand atrium 2a, which may amount to up to 100 mm Hg.

The medical apparatus according to the third embodiment effectively prevents the pressure increase in the left-hand atrium 2a from propagating into the pulmonary veins 4b, 4b', 4c, 4c'. More specifically, it is provided that the medical apparatus comprises a total of four valves 10a to 10d, with each of the four valves 10a to 10d being assigned to a pulmonary vein 4b, 4b', 4c, 4c'.

Similar to the first embodiment of the medical apparatus, the individual valves 10a to 10d of the embodiment shown in FIG. 3 are supported by way of stents 12a to 12d in the respective mouth areas of the pulmonary veins 4b, 4b', 4c, 4c' which lead into left-hand atrium 2a.

Figure 4:
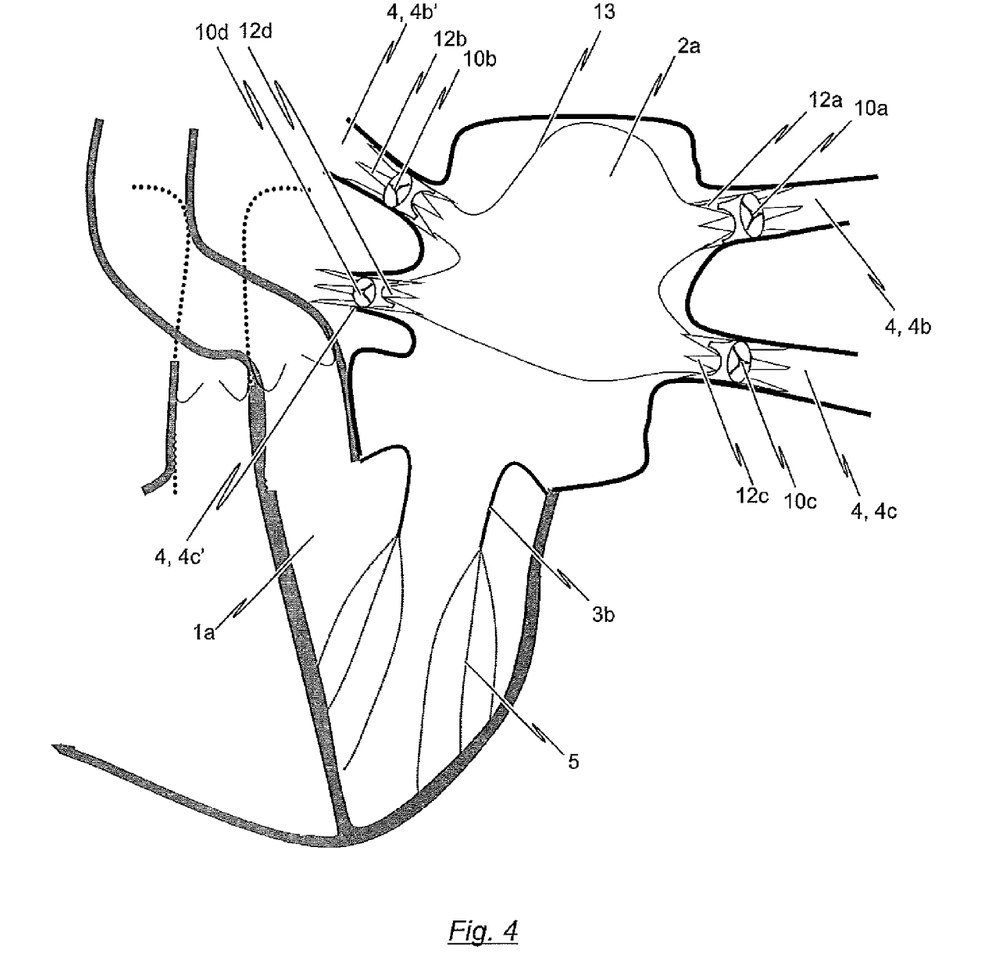
FIG. 4 is a schematic view of a fourth embodiment of the inventive medical apparatus, which is specifically suited for the therapeutic treatment of a mitral insufficiency.

In FIG. 4, another embodiment of a medical apparatus for the therapeutic treatment of a mitral insufficiency is shown. The embodiment of the medical apparatus of FIG. 4 is essentially identical to the previously described embodiment shown in. 3. However, in the fourth embodiment, the individual stents 12a to 12d are connected with each other via supporting braces 13. As has already been explained in the context of FIG. 2, these supporting braces 13 are used to hold the stents 12a to 12d, in particular during systole, in their respective implantation site.

Figure 5:
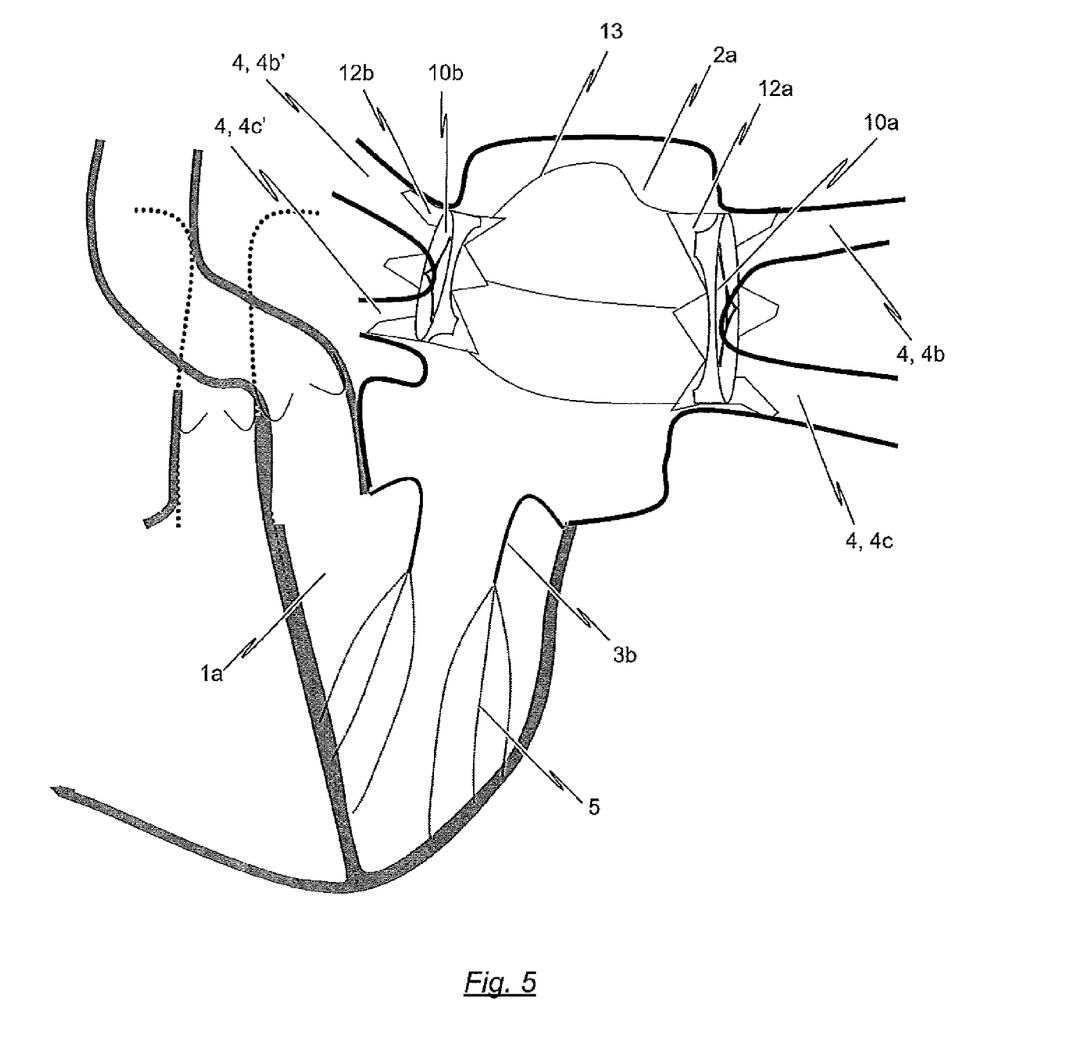
FIG. 5 is a schematic view of a fifth embodiment of the inventive medical apparatus, which is specifically suited for the therapeutic treatment of a mitral insufficiency.

In FIG. 5, a yet further embodiment of a medical apparatus for the therapeutic treatment of a mitral insufficiency is shown. In contrast to the previously described embodiment with reference to FIG. 4, a total of only two valves 10a, 10b are employed. Each of the two valves 10a, 10b prevents regurgitation of blood from the left-hand atrium 2a of the heart into two neighbouring pulmonary veins 4b, 4b' or 4c, 4c', respectively.

Although it would be principally conceivable to suture the valves 10a, 10b at the implantation site, a stent 12a, 12b is ideally employed for each valve 10a, 10b in the embodiment shown in FIG. 5. The valves 10a, 10b fastened into the stent 12a, 12b is suitably positioned and secured upstream of the two mouth openings of the pairs of pulmonary veins 4b, 4b' or 4c, 4c', respectively.

Although the above description of the embodiments refer to several stents which are used for the positioning and fixing of the valve means, it is, of course, also conceivable that only one individual stent is used for the medical apparatus. Such an apparatus may comprise several stent portions which are, for example, connected to each other via supporting braces, with each stent portion being assigned at least one valve means. Each stent portion will also be designed to be implanted into a vein of the venous system which leads into an atrium of the heart.

As already mentioned, it is also possible to use one or several self-expandable stents 12. The stent 12 may, for example, comprise an integral structure which is cut from a small metal tube by means of a laser. Subsequently, the structure may be subjected to a suitable forming and heat treatment process so that the stent can be transferred form a folded configuration during implantation to an expanded configuration once at the implantation site. This forming and heat treatment process should advantageously be performed in a stepwise manner to avoid damage to the stent structure.

It is, of course, also conceivable to use a stent structure consisting of a braid of thin wires or threads.

In a particularly preferred realisation of the medical apparatus, it comprises at least one stent 12 with the valve 10 fastened thereto with valve means 10 comprising mechanical valve flaps 11 made from a synthetic material, a metal, or an organic material.

With respect to the material to be used for the stent 12 of the medical apparatus, a shape memory material is preferably. This provides the stent 12, under the influence of an external stimulus, to transform from a temporary shape to a permanent shape, with the temporary shape prevailing in the first forming operation of the stent, i.e. in the folded condition of the medical apparatus, and the permanent shape prevailing in the second forming operation of the stent, i.e. in the expanded condition of the medical apparatus. In particular, by using a shape memory material, such as nitinol—an equiatomic alloy of nickel and titanium—it is possible to implant the medical apparatus in a particularly gentle, non-abrasive and non-invasive manner In the manufacture of a stent 12 from a shape memory material it may be provided that, after cutting the stent structure from a small metal tube, the structure is deformed and fixed in desired temporary shape. This procedure is known as "programming". This process may, on the one hand, be carried out in such a manner that the stent structure is heated, deformed, and then cooled. On the other hand, the stent structure may also be deformed at a low temperature, which is known as "cold drawing". In this operation, the permanent shape is stored, while the temporary shape is currently present. If the stent structure is subsequently subjected to an external stimulus, the shape memory effect will be initiated and thus the stored permanent shape be restored. By cooling of the stent structure, the temporary shape will be restored non-reversibly, which is referred to as a so-called "one-way shape memory effect". The original temporary shape—but other shapes as well—may be reprogrammed by another mechanical deformation.

In a particularly preferred embodiment it is provided that the external stimulus is a specifiable transition temperature. It is therefore conceivable that, for initiating the shape memory effect and thus for restoring the stored permanent shape of the stent 12, the stent material has to be heated to a temperature above the transition temperature. By suitably selecting the chemical composition of the shape memory material, a certain transition temperature can be established in advance.

It is particularly preferred to establish the transition temperature in the range of the room temperature and the body temperature of the patient. This is advantageous primarily with respect to the application field of the medical apparatus as an implant in a body of a patient. In the implantation of the medical apparatus, the only precaution that has to taken is to ensure that the instrument is heated to the body temperature (36° C.) of the patient in the implanted condition only, and thus the shape memory effect of the stent material is initiated.

The invention is not limited to the characteristics which have been described in connection with the embodiments illustrated in the figures, but allows any combination of the characteristics indicated in specification.

LIST OF REFERENCE NUMERALS 1a left-hand ventricle
1b right-hand ventricle
2a left-hand atrium
2b right-hand atrium
3a tricuspid valve
3b mitral valve
4 vein system
4a upper vena cava
4a' lower vena cava
4b first pulmonary vein
4b' second pulmonary vein
4c third pulmonary vein
4c' pulmonary vein
5 tendinous fibres
6 aorta
7 pulmonary artery
8a pulmonary semilunar valve
8b aortic semilunar valve
10 valve/valve means
11 valve flap
12 stent
13 supporting brace

The invention claimed is:

1. An apparatus for treating regurgitation deficiencies of an atrioventricular valve located between a ventricle of a heart and an atrium of the heart, comprising:
   a first stent, having a first valve attached thereto, for implantation at least partially within a first vein leading to the atrium;
   a second stent, having a second valve attached thereto, for implantation at least partially within a second vein leading to the atrium;
   a third stent, having a third valve attached thereto, for implantation at least partially within a third vein leading to the atrium; and
   a fourth stent, having a fourth valve attached thereto, for implantation at least partially within a fourth vein leading to the atrium;
   wherein the first stent is structurally unconnected from the second stent, and the third stent is structurally unconnected from the fourth stent.

2. The apparatus of claim 1, wherein
   the first and third valves permit blood flow towards the atrium from the first and third veins, respectively, and prevent blood flow from the atrium to the first and third veins, respectively, when implanted; and
   the second and fourth valves permit blood flow towards the atrium from the second and fourth veins, respectively, and prevent blood flow from the atrium to the second and fourth veins, respectively, when implanted.

* * * * *